United States Patent
Kube et al.

(10) Patent No.: US 10,405,885 B2
(45) Date of Patent: Sep. 10, 2019

(54) MEDICAL APPLICATOR

(71) Applicant: Roche Diabetes Care, Inc., Indianapolis, IN (US)

(72) Inventors: Oliver Kube, Worms (DE); Michael Orth, Grossniedesheim (DE); Helmut Walter, Heppenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1008 days.

(21) Appl. No.: 14/818,650

(22) Filed: Aug. 5, 2015

(65) Prior Publication Data
US 2016/0038180 A1 Feb. 11, 2016

(30) Foreign Application Priority Data
Aug. 5, 2014 (EP) .................................... 14179911

(51) Int. Cl.
| | | |
|---|---|---|
| A61B 17/34 | (2006.01) | |
| A61B 5/00 | (2006.01) | |
| A61B 5/145 | (2006.01) | |
| A61B 17/30 | (2006.01) | |

(52) U.S. Cl.
CPC ...... *A61B 17/3468* (2013.01); *A61B 5/14503* (2013.01); *A61B 5/14532* (2013.01); *A61B 5/6832* (2013.01); *A61B 17/34* (2013.01); *A61B 2017/308* (2013.01); *A61B 2217/005* (2013.01); *A61B 2503/40* (2013.01); *A61B 2560/045* (2013.01); *A61B 2560/063* (2013.01); *A61B 2562/242* (2013.01)

(58) Field of Classification Search
CPC .. A61M 37/0015; A61B 5/145; A61B 5/6832; A61B 17/34
See application file for complete search history.

(56) References Cited

U.S. PATENT DOCUMENTS 6,537,242 B1 * 3/2003 Palmer .............. A61M 37/0015
600/309
8,515,519 B2   8/2013 Brister et al.
2008/0242962 A1  10/2008 Roesicke et al.

FOREIGN PATENT DOCUMENTS

| EP | 2668901 A1 | 12/2013 |
| WO | 199625088 A1 | 8/1996 |
| WO | 200839944 A2 | 4/2008 |

* cited by examiner

*Primary Examiner* — Eric F Winakur

(57) ABSTRACT

A medical applicator and a manipulation unit for use in connection with specific variants of the medical applicator are disclosed. In general, the medical applicator has an insertion needle (108; 308) configured for puncturing a part of a human or animal body (B), a sensor assembly (110; 310) configured to be at least partially inserted into a human or animal body (B) when the body is punctured by said insertion needle (108; 308) and a lifting means (102; 301, 302) for lifting up a surface adjacent portion of the human or animal body (B) towards the insertion needle (108; 308).

14 Claims, 4 Drawing Sheets

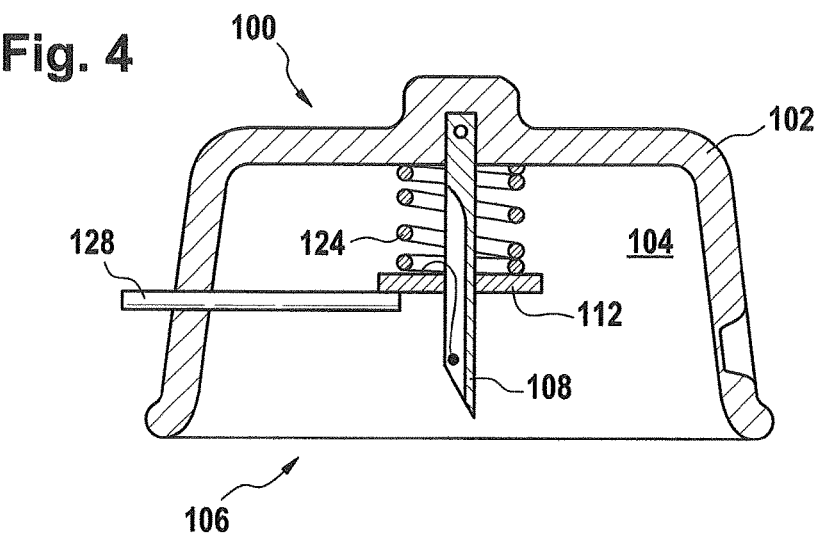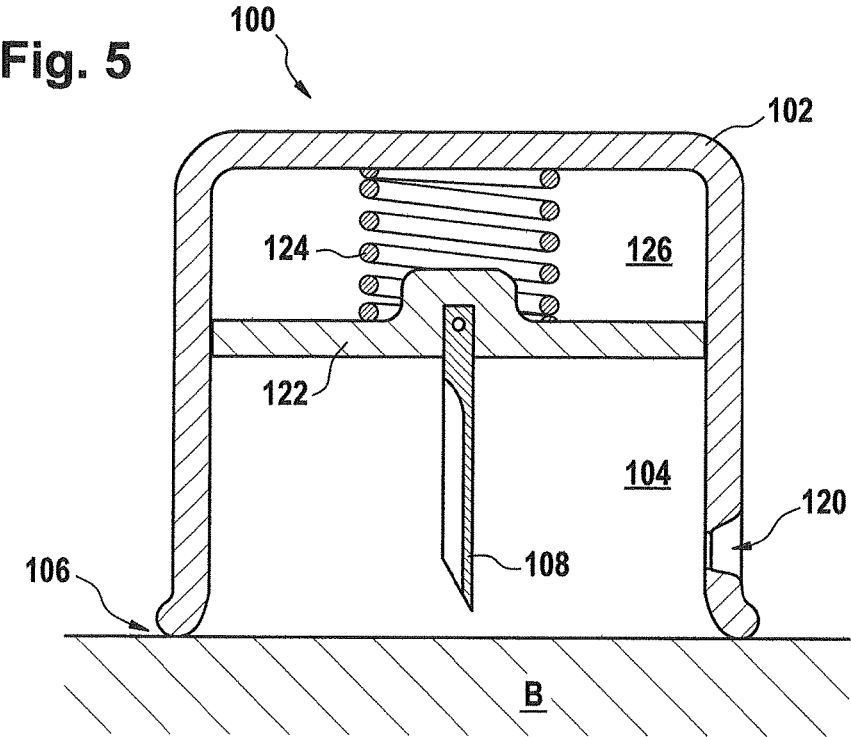

MEDICAL APPLICATOR

CROSS-REFERENCES TO RELATED APPLICATIONS

This application claims priority to European patent application No. 14 179 911.4, which was filed on Aug. 5, 2014. This reference is incorporated by reference herein in its entirety.

FIELD OF THE INVENTION

The invention relates to an apparatus for insertion of a medical sensor or probe for in vivo monitoring of an analyte in a human or animal body and in particular to a medical applicator for inserting a transcutaneous analyte sensor into a subcutaneous region of a human or animal body.

BACKGROUND AND RELATED ART

For the proper management of chronic health conditions in human or veterinarian medicine it may be crucial to periodically monitor one or more analyte levels in the blood stream or interstitial fluid of a subject. In the case of diabetes mellitus the patient routinely monitors the glucose levels to avoid hypoglycemic episodes and hyperglycemic episodes. For other situations where health monitoring is important, other analytes, such as lactate or oxygen, may be measured.

A number of approaches have been developed for continuous or periodic monitoring of the analyte concentration by means of a medical probe to be implanted into a human or animal body. For instance, an electrochemical sensor may be inserted into a subcutaneous tissue region of the subject where the analyte concentration is continuously monitored and/or logged.

For instance publication US 2008/0242962 A1 discloses a monitoring system for monitoring analyte concentration, such as glucose, with an implantable sensor. The implantable sensor is configured to generate measurement signals which are compressed through statistical techniques to produce compressed measurement data that may be easier to process and communicate. A base station carries the implantable sensor along with a signal processor, a memory, and a transmitter. A display device is also disclosed that can receive the compressed measurement data from the base station for further processing and display.

As another example, publication U.S. Pat. No. 8,515,519 B2 discloses a transcutaneous analyte sensor assembly to be mounted on a skin of a host with a first side of the housing. The housing further comprises a sensor electronics unit having one or more electrical contacts, wherein the sensor electronics unit is configured to releasably mate with a second side of the housing opposite to the first side such that the one or more electrical contacts of the housing electrically connect with the one or more electrical contacts of the sensor electronics unit. The sensor is configured to continuously and/or intermittently measure a level of an analyte in a tissue of the host. The sensor further comprises one or more electrical contact points configured to electrically connect to the electrical contacts of the sensor electronics unit via the electrical contacts of the housing when the sensor electronics unit is mated to the housing. Additionally, the housing is configured to continuously support the sensor within the tissue of the host during a time period of continuous or intermittent measurement.

As another example, publication WO 2008/39944 A2 discloses devices and methods for positioning a portion of a sensor at a first predetermined location, displacing the portion of the sensor from the first predetermined location to a second predetermined location, and detecting one or more signals associated with an analyte level of a patient at the second predetermined location are disclosed.

As another example, publication WO 96/25088 A1 discloses an insertion set for transcutaneous placement of a sensor such as a glucose sensor at a selected site within the body of a patient. The insertion set comprises a slotted insertion needle extending through a mounting base adapted for mounting onto the patient's skin. A flexible thin film sensor includes a proximal segment carried by the mounting base and defining conductive contacts, unnumbered, adapted for electrical connection to a suitable monitor, and a distal segment protruding from the mounting base with sensor electrodes for transcutaneous placement. The distal segment of the sensor extends within a protective cannula, a portion of which is slidably disposed within the insertion needle. Placement of the mounting base onto the patient's skin causes the insertion needle to pierce the skin for transcutaneous placement of the cannula with the sensor therein.

Finally, publication EP 2 668 901 A1 discloses a sensor insertion assembly including a sensor cartridge. The sensor cartridge comprises an insertion needle and a sensor within a sterile capsule. The sensor insertion assembly further comprises an inserter having a chamber for receiving the sensor cartridge, wherein the inserter further comprises an insertion mechanism operable for actuating the insertion needle for inserting the sensor into a subject. The sensor cartridge is removable from the chamber. The sensor cartridge is operable for shielding the insertion needle upon removal of the sensor cartridge from the chamber.

It is an object of the invention to provide an improved medical applicator and a respective manipulation unit.

SUMMARY OF THE INVENTION

The invention provides for a medical applicator for insertion of a sensor assembly into a human or animal body, and a manipulation unit according to the independent claims. Various embodiments and enhancements thereto are given in the respective dependent claims.

A principal medical applicator comprises an insertion needle being configured for puncturing a part of a human or animal body, a sensor assembly being configured to be at least partially inserted into the human or animal body when being punctured by the insertion needle, and lifting means for lifting up a surface adjacent portion of the human or animal body towards the insertion needle so that the sensor assembly is at least partially inserted into the human or animal body.

This may advantageously allow an operation wherein the soft skin and subcutaneous tissue is displaced away from the underlying muscular tissue for puncturing and thereby may help in avoiding injury thereof.

This may avoid a disadvantage of known systems for inserting trans-/subcutaneous sensor systems. These often require correct handling and therefore should be used by professional health personnel only. Especially diabetes patients mainly are aged persons and therefore often lack manual skills necessary for using prior art applicators. Additionally, patients are in expectation of pain reluctant to perform the insertion themselves in a well-controlled manner.

In an embodiment, the medical applicator has lifting means comprising a container member defining a cavity and an orifice, the cavity being configured for receiving the sensor assembly, the insertion needle being located within the cavity at a recessed position relative to the orifice and being configured for puncturing a part of the human or animal body entering through the orifice, the lifting means further comprising means for applying underpressure to the cavity for taking, through the orifice, an adjacent portion of the human or animal body into the cavity by suction.

Suction based operation may have the advantage of equilibrated and widely-spread force application and may help avoiding hematoma and unintentional injury of skin and/or subcutaneous tissue.

In a more specific embodiment, the means for applying underpressure to the cavity comprise a suction port formed in an exterior wall of the container member.

In a much more specific embodiment, the suction port is defined by a predetermined braking point in an exterior wall of the container member.

In an embodiment, the cavity of the medical applicator has the shape of a dome or ventouse.

In an embodiment, the medical applicator is configured to allow displacement of the insertion needle relative to the orifice towards the adjacent portion of the human or animal body.

This, in instances, may advantageously allow performing insertion at a more moderate underpressure and thereby may help avoiding hematoma and skin irritation.

In an embodiment, the container member of the medical applicator comprises a deformable section connecting the orifice to the mount of the insertion needle for allowing displacement of the insertion needle relative to the orifice by application of a deformation force to the container member. In a more specific embodiment, the deformable section may be provided in the shape of a bellow and, in particular, in the shape of a flat and/or cylindrical bellow.

This, in instances, may advantageously allow fabrication in a single part and avoid cost and efforts for assembly.

In a more specific embodiment, the medical applicator has the insertion needle being slidably movable relative to the container member.

In a more specific embodiment, the insertion needle is supported by a piston member, whereby the piston member being slidably movable within a section of the container member and being exposable to an actuating force by means of a biased elastic member and/or by application of the underpressure.

In a more specific embodiment, the sensor assembly of the medical applicator comprises an external device being configured to remain outside the human or animal body after deployment of the sensor assembly.

In a more specific embodiment, the external device has at least one self-adhesive surface portion facing towards the orifice.

In a more specific embodiment, the external device is admittable to the application force by means of the biased elastic member and/or by application of the underpressure for deployment of the external device to the surface of the human or animal body.

This, in instances, may advantageously strengthen and improve adhesive bonding between the skin surface of the human or animal body and the bottom surface of the external device.

In a more specific embodiment, the external device is releasably fixed in a biased pre-deployment position.

In a more specific embodiment, the fixation of the external device is releasable by deformation of a portion of the container member and/or by retraction of retention pins.

In a more specific embodiment, the medical applicator includes a sealing member extending over the orifice to cover the cavity.

In a more specific embodiment, the cavity of the medical applicator contains a protective atmosphere to avoid degradation of the self-adhesive surface portion.

In an alternative more specific embodiment, the sealing member comprises a protective liner adapted for protecting the self-adhesive surface portion of the external device.

A principal manipulation unit for facilitating utilization of a medical applicator comprises a fitting for engagement with the medical applicator and means for generation of the underpressure and/or means for applying a force to the container member of the medical applicator received in the fitting for effecting deformation thereof.

In an embodiment, the means for generation of underpressure comprises an electric vacuum pump.

In an embodiment, the fitting of the manipulation unit is configured as a suction holder.

In an embodiment, the manipulation unit further comprises puncturing means for puncturing the container member of the medical applicator received in the fitting to form the suction port for the application of the underpressure.

In an embodiment, the manipulation unit additionally comprises progress sensor means for detecting the presence of a portion of the human or animal body at an internal location within the cavity of the medical applicator and generating a signal descriptive thereto.

In an embodiment, the progress sensor means of the manipulation unit comprises an optical detection device, especially an infrared radiation or image sensor device.

In an embodiment, the manipulation unit has an electronic controller configured for operating the vacuum pump in response to the signal of the progress sensor means.

In an alternative embodiment of the principal medical applicator, the lifting means include pincer arms configured for creating an upwardly bending movement of the skin and subcutaneous tissue of the human or animal body towards the insertion needle.

BRIEF DESCRIPTION OF THE DRAWINGS

In the following exemplary implementations of a medical applicator and a manipulation unit are explained in greater detail, by way of example only, making reference to the drawings wherein:

FIG. 4 shows a schematic sectional view of a second exemplary embodiment of a medical applicator;

FIG. 5 shows a schematic sectional view of a third exemplary embodiment of a medical applicator;

DETAILED DESCRIPTION

Like numbered elements in these figures are either equivalent elements or perform the same function. Elements which have been discussed previously will not necessarily be discussed in later figures if the function is equivalent.

Figure 1:
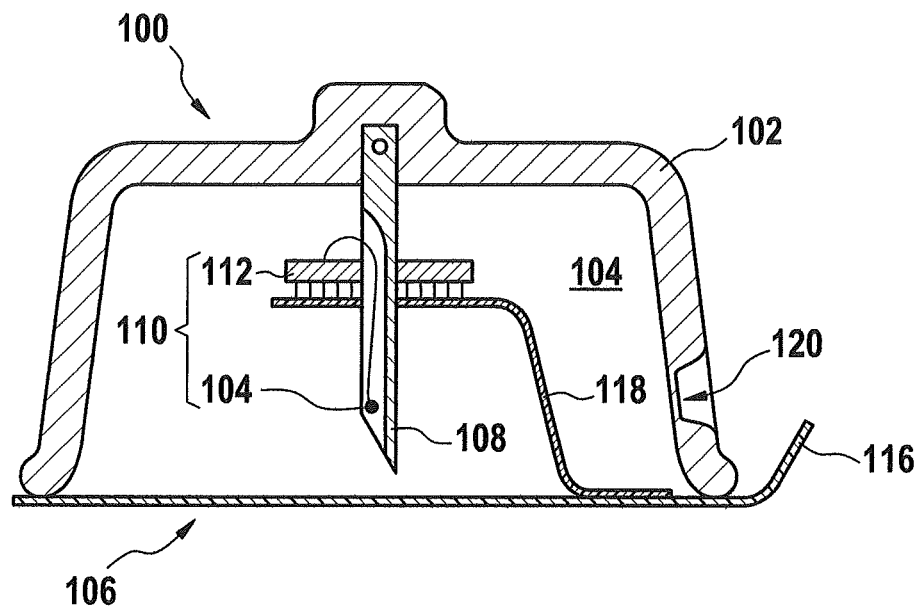
FIG. 1 shows a schematic sectional view of a first exemplary embodiment of a medical applicator.

According to FIG. 1, a first exemplary configuration of a medical applicator may have a container member 102. The container member 102 may define a cavity 104 and an orifice 106. Preferably, the container member 102 may be dome shaped, as shown. The cavity 104 may, for example, be configured to receive a sensor assembly and, in particular, a transcutaneous analyte sensor assembly 110 to be applied to a human or animal body B.

In instances, an insertion needle 108 may be provided at a fixed mount located inside the cavity 104. In a particular situation, the container member 102 may be made from a thermoplastic resin whereby the insertion needle may be molded into a mount portion. In instances, the insertion needle 108 may have the tip located at a recessed position behind the orifice 106. Additionally, the insertion needle 108 may be aligned to project from the interior of the cavity 104 towards the orifice 106.

In instances, the insertion needle 108 may have a longitudinal groove for receiving a sensor wire, a probe tube or the like. In particular, the insertion needle 108 may be a grooved needle or hollow needle with a cross-section that has been removed. In a more detailed example, the insertion needle 108 may have a C-shape or V-shape cross-section. This may enable the insertion needle 108 to partially insert the transcutaneous analyte sensor assembly 110 and then remove the needle while leaving the sensor within the human or animal body. At this point it should be noted that the diameter of the insertion needle 108 has been considerably exaggerated throughout all schematic drawings.

The transcutaneous analyte sensor assembly 110 may be located within the cavity 104 at an internal position distant from the orifice 106. The transcutaneous analyte sensor assembly 110 may include an external device 112 configured to remain outside the human or animal body B after application, preferably in contact to the skin surface. The external device 112 may have a flat bottom surface coated with an adhesive for fixation. The transcutaneous analyte sensor assembly 110 may have a probe portion to be at least partially inserted into the subcutaneous tissue of human or animal body B via a channel through the skin.

In the case of electrical analyte sensing, the probe portion may include an electrical sensor 114 at a distal position and a wiring for providing connection to the external device 112. This mainly corresponds to the typical configuration of transcutaneous analyte sensor assemblies known from the prior art as cited before and therefore will not be explained in more detail.

In instances, the external device 112 of the sensor assembly 110 may comprise a through hole or slot for adjustment and/or fixation on the insertion needle 108. The through hole or slot may be designed for slightly frictional clamping or engagement with the insertion needle 108, as shown. The frictional clamping force may be chosen such as to allow the external device 112 to be pulled away from the insertion needle 108 by effect of an adhesive force applicable to the underside of the external device 112 when fixed by adhesion to the skin of a human or animal body. In an alternative or cumulative enhancement, mechanical and/or adhesive means for fixation of the external device 112 to the skin of a human or animal body might be provided inside the cavity 104.

A sealing member 116 may be provided to tightly extend over the orifice 106 as a closure to the cavity 104. The closure may help to avoid contamination of the transcutaneous analyte sensor assembly 110 and the insertion needle 108 during stock and transport of the medical applicator 100. In instances, the sealing member 116 may be equipped with an additional protective liner 118 which is configured to prevent the adhesive on bottom surface of the external device 112 from degradation during stock and transport. In more particular examples, the protective liner 118 may be a flexible strip extending over the adhesive and having an end portion connected to an inner portion of the sealing member 116, as shown. In such situation, removal of the sealing member 116 will cause the flexible strip to be peeled from the adhesive in a single action. In an alternative, the adhesive on the bottom surface of the external device 112 might be protected by means of a protective gas charge contained in the cavity 104. Then, there would be no need for additional protective coverage. In another alternative, the sealing member 116 might be provided in a configuration of a rigid sealing cap. The sealing cap might be provided in a configuration of twist-off sealing cap to facilitate unlocking and removal from the container member 102. The sealing cap might be provided with a central stiff portion protruding into the cavity 104 and having a flat portion covering the adhesive on bottom surface of the external device 112. The stiff portion of the sealing cap might be configured to serve as a protection sleeve for the insertion needle 108. These embodiments are not shown in the drawings.

In instances, the container member 102 may have a suction port 120 formed in an exterior wall thereof. In such situation, the suction port 120 may be used for applying vacuum or underpressure to the cavity 104 to effect at least partial evacuation thereof. In more detailed examples, the suction port 120 may be provided with a removable closure or coverage to avoid contamination of the cavity 104 and/or insertion needle 108 through this passage to the exterior. The removable closure of the suction port 120 may have the form of an integrally made stitch-through membrane portion or diaphragm in the exterior wall 120. There may be provided a section having reduced thickness in the exterior wall, as shown. This may allow the suction port 120 to be easily formed by punching this section with a lancet or an edged suction nozzle of an evacuation pump or vacuum device. The suction port might be formed initially as a through hole in the container member 102. In such situation, another closure member might be provided as a cover to the suction port for avoiding contamination of the cavity 104 and/or insertion needle 108 via the suction port 120.

Figure 2:
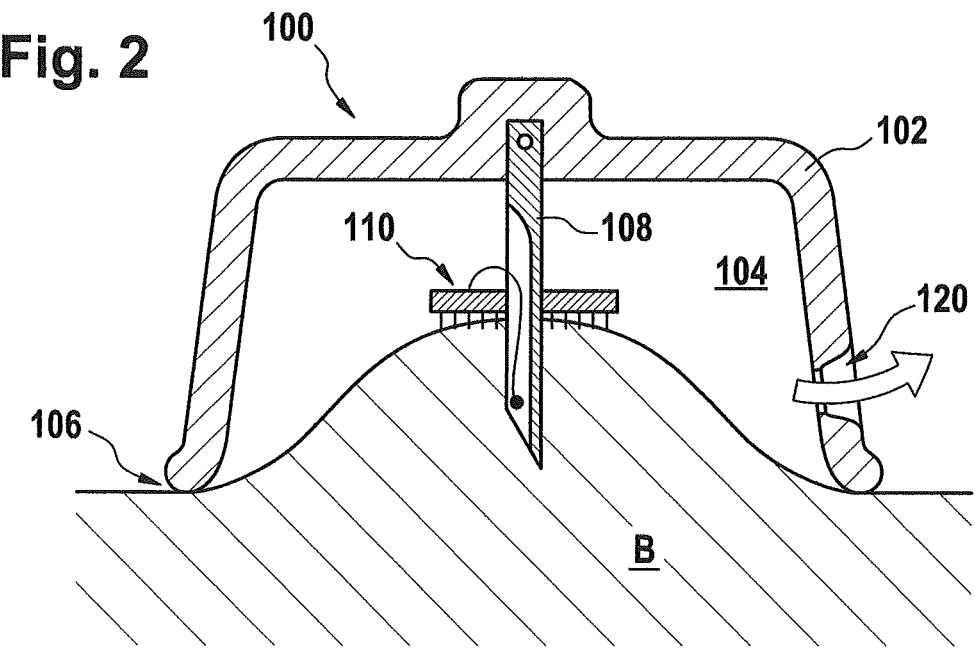
FIG. 2 shows a schematic sectional snapshot of a typical operation condition for the exemplary embodiment of a medical applicator according to FIG. 1.

According to FIG. 2, after removal of the sealing member 116, the medical applicator 100 may be positioned onto the skin of a human or animal body B in a position wherein the orifice 106 having tightly annular contact to the skin surface. Afterwards or before application, the suction port 120 of the container member 102 may be opened as described before. Subsequently, via the open suction port 120 vacuum or underpressure may be applied to the cavity 104 for at least partial evacuation thereof. Annular contact between orifice 106 and skin surface will prevent cavity 104 from being vented through orifice 106. As pressure in cavity 104 decreases, the skin and underlying subcutaneous tissue of the human or animal body B adjacent to orifice 106 will become pushed into cavity 104 by outer pressure. In the same way, the applicator 100 as a whole will be pressed onto the human or animal body B due to outer pressure. Continued evacuation of the cavity 104 may throw up a limited surface adjacent portion of the human or animal body (B) against the insertion needle 108. This may be used to bring the skin into contact with the insertion needle 108 and, subsequently, to perform puncturing of the skin and subcutaneous tissue of the human or animal body B by the insertion needle 108. Further decrease in cavity pressure then may cause the skin surface to lie against the bottom surface of the external device 112. In such situation, the adhesive provided on the bottom surface of the external device 112 as explained before may cause fixation of the external device 112 to the skin surface of the human or animal body B. Afterwards, the cavity 104 may be vented via the suction port 120. Then, the skin and/or subcutaneous tissue formerly drawn into cavity 104 by suction may relax into its initial shape by internal elasticity. If, as explained before, adhesive bonding has been established between the skin and the external device 112 this may cause the transcutaneous analyte sensor assembly 110 to be extracted from the cavity 104 of the applicator 100 in course of venting. After venting has been completed, the empty container member 102 of the medical applicator 100 may be removed from the human or animal body B. For avoidance of unintentional removal, the transcutaneous analyte sensor assembly 110 may be covered by a plaster or similar well-known protection. Finally, the empty container member 102 of the medical applicator 100 may be disposed or collected for remanufacturing.

Figure 3:
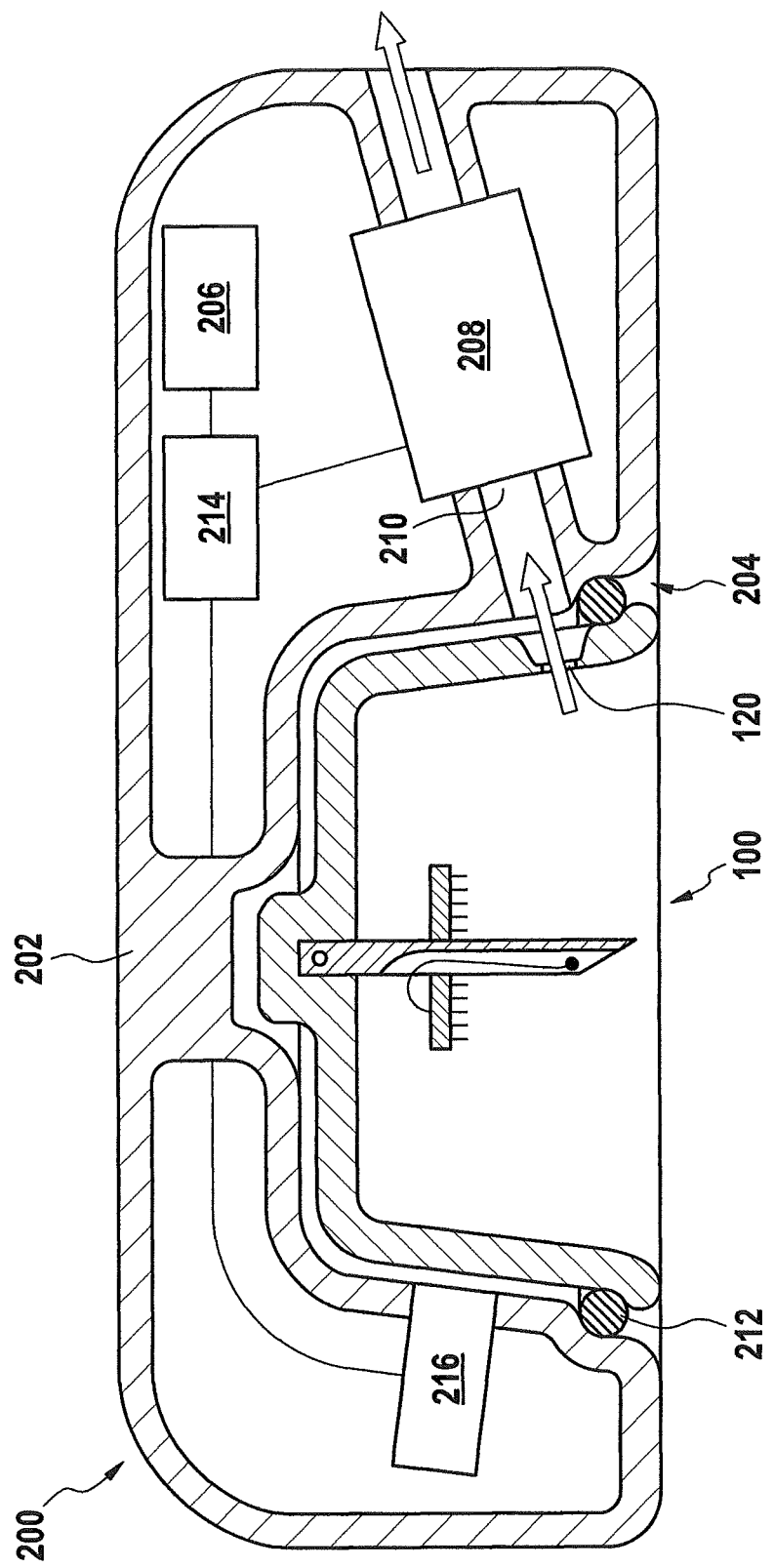
FIG. 3 shows a schematic sectional view of an exemplary embodiment of a reusable manipulation unit.

Use of the medical applicator 100 as described before may be facilitated by means of a manipulation unit 200 according to FIG. 3. In instances, the manipulation unit 200 may have a casing 202 equipped with a fitting 204 configured to receive a medical applicator 100. Further, there may be a battery 206 operated electrical vacuum pump 208 arranged in the casing 202 of the manipulation unit 200. The vacuum pump 208 may be connected to a port 210 inside the fitting 204. The port 210 may be located to match with the position of the suction port 120 of a medical applicator 100 when correctly inserted into the fitting 204. Additionally, the vacuum pump 208 may include means for opening the suction port 120 of the medical applicator 100 before evacuation. In a more particular example, the suction port 120 of the medical applicator 100 may be opened by perforation of a thin-walled portion of the container member 102 as explained before. Accordingly, the manipulation unit 200 may comprise a perforation means as a punch or lancet, for example.

In instances, the manipulation unit 200 may have a sealing gasket 212 configured to surround the container member 102 of the medical applicator 100 when correctly inserted into the fitting 204. Thus, the sealing gasket 212 may serve to prevent external air to bypass into the fitting 204 thereby causing loss or degradation of vacuum generated by vacuum pump 208 via port 210. In instances, the manipulation unit 200 may additionally comprise means for enabling at least semi-automatic operation. There may be an electronic controller 214 included in the casing 202. The electronic controller 214 may be battery 206 operated and configured to control operation of the vacuum pump 208. In enhancement thereof, progress sensor means 216 may be configured inside the fitting 204 to provide the electronic controller 214 with a signal significant for a certain stage of operation. The progress sensor means 216 may include, for example, a sensor configured for detection of the skin of a human or animal body B entering into the cavity 104 of the medical applicator 100 received in the fitting 204. In more detail, the progress sensor means 216 may include an optical sensor as, for example, a photoelectrical barrier or the like. In an enhancement, the electronic controller 214 may be configured to terminate operation of the vacuum pump 208 in response to receiving a signal from the progress sensor means 216. As another enhancement, the electronic controller 214 may be configured to switch the vacuum pump 208 to a reverse operation mode afterwards for venting the cavity 104 of the medical applicator 100 received in the fitting 204. The electronic controller 214 may be configured to stop reverse operation of the vacuum pump 208 after a predetermined time period has lapsed. The electronic controller 214 may provide the user of the manipulation unit 200 with a signal upon termination of operation as an indication to remove the empty container member 102 of the medical applicator 100 from the fitting 204. Preferably, this signal may be vibrational, optical and/or visual.

Figure 6:
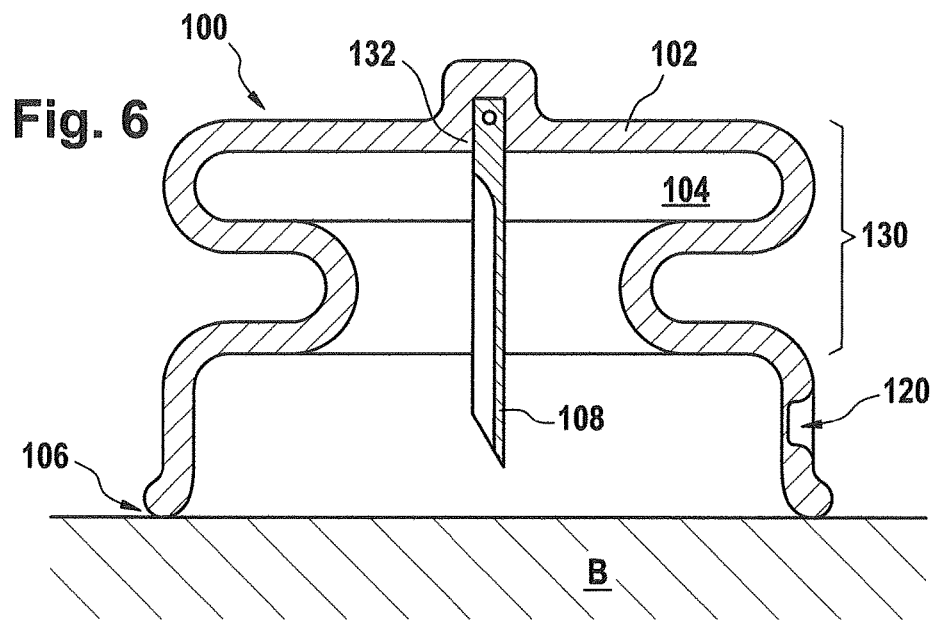
FIG. 6 shows a schematic sectional view of a fourth exemplary embodiment of a medical applicator.

According to FIGS. 4, 5 and 6 various modifications may be made to the medical applicator 100 for a number of purposes thereby maintaining the operational principle and the interoperability with the manipulation unit according to FIG. 3 based thereon.

In particular, according to FIG. 4, in a second exemplary embodiment of a medical applicator 100, a spring 124 or any other kind of elastic member may be provided for biasing the external device 112 of the transcutaneous analyte sensor assembly 110 in a direction outwardly respective to cavity 104. Biasing force may advantageously be used to improve deployment of the external device 112. Additionally, such biasing force may advantageously increase the contact pressure between the bottom surface of the external device 112 and the skin surface of the human or animal body B thereby strengthening a potential adhesive fixation, if present. Releasable fixation means may be provided for securing of the external device 112 in a pre-deployment position. In an exemplary situation, the releasable fixation means may be implemented as a number of retractable retention pins 128. The retention pins may extend through an outer wall of the container member 102 into the cavity 104 thereby allowing actuation from outside the cavity 104, as shown. In instances, retraction may be performed manually, preferably at a certain stage during deployment of the sensor device 110. A user may retract the retention pins 128 before venting the cavity 104 to thereby enable the external device to 112 follow the relaxation of the portion of the human or animal body.

In an alternative exemplary situation, not shown in the drawings, the releasable fixation means may be implemented as retractable fixation clips inside the cavity 104. Advantageously, the fixation clips may be formed integrally with the container member 102. The container member 102 may be configured to release the fixation clips when being subject to a deformation. The required deformation of the container member 102 may be effected as a result of the pressure difference in course of a deployment operation as explained before with reference to FIG. 2. The container member 102 may have an approximate ellipsoidal shape in a cross-section perpendicular to the insertion needle 108 at the height of the clips whereby the semi-major axis may lie in the plane of the drawing sheet. In such configuration, lowering the pressure inside the cavity 104 may cause the container member 102 to flatten along the semi-minor axis. Flattening in one direction, however, may cause the container member 102 to stretch along the semi-major axis at the same time. This may be used for driving the fixation clips away from each other thereby unengaging from the external device 112. As a result, the external device 112 may be released from the fixation clips. A biasing force may push the external device 112 towards the orifice 106 afterwards. In a more elaborated example, the stiffness of the container member 102 may be designed to perform releasing of the fixation clips at the end of evacuation.

According to FIG. 5, in a third exemplary embodiment of a medical applicator 100, another improvement may be given by means to enable relative displacement of the insertion needle 108 respective to the container member 102 or, more particularly, to the orifice 106 during a deployment operation. In a more specific example thereof, the insertion needle 108 may be mounted on a piston or slider 122. In a similar situation, the container member 102 may be configured to allow displacement of the piston or slider 122 to a certain extent. Typically, displacement will be limited to a direction approximately parallel to the insertion needle's 108 longitudinal dimension. The container member 102 may have a cylindrical guidance section to restrict movement of the piston or slider 122 to a linear travel, as shown. The piston 122 may be gas-tightly received in the guidance section. This will enable gas pressure driven displacement during deployment operation. The piston 122 may be configured to separate a predetermined gas volume 126 from the cavity 104. This separated gas volume 126 may act as an elastic member thereby causing the piston 122 to displace towards the orifice 106 during evacuation of the cavity 104 via the suction port 120. In exemplary configurations, displacement of the piston 122 may cause the insertion needle 108 to be driven towards punctuation of the human or animal body B adjacent to the orifice 106. This may advantageously result in faster deployment operation and may additionally allow performing punctuation at a lower pressure difference. As another improvement, a spring 124 or any similar elastically structural member may be provided to replace and/or support the effect of the gas pressure difference as described before. However, it may be considered as an obvious advantage of a mainly gas pressure difference driven displacement of the insertion needle 108 to depend on tight closure of the orifice 106. As a consequence, an unintentional application of vacuum or underpressure to the medical applicator 100 without a tight contact to a human or animal body B will not cause the insertion needle 108 to be pushed towards the orifice 106. In some specific implementations, this may be used as an inherent security feature.

According to FIG. 6, a fourth exemplary embodiment of a medical applicator 100 may have the container member 102 provided with an elastic section as, for example a flat and/or cylindrical bellow. In the exemplary situation, the cylindrical bellow may be formed in a cylindrical section between the needle mount 132 and the orifice 106. In the exemplary situation according to FIG. 6, for the sake of simplification, the number of beadings in the bellow has been reduced to two, namely a positive, outwardly projecting beading in the upper region which smoothly fades into a negative, inwardly projecting beading in the lower section. It has to be understood that in most practical situations, there may be a need for a larger number of beadings in order to reduce the depth of the beadings thereby maintaining the degree of elasticity and extensibility of the entire bellow. Additionally, in practice, the spring rate of the bellow 130 may be adjusted to prevent it from significantly compressing until the amount of underpressure in the cavity 104 has reached a value sufficient for taking the body portion B into to the required extent.

Figure 7:
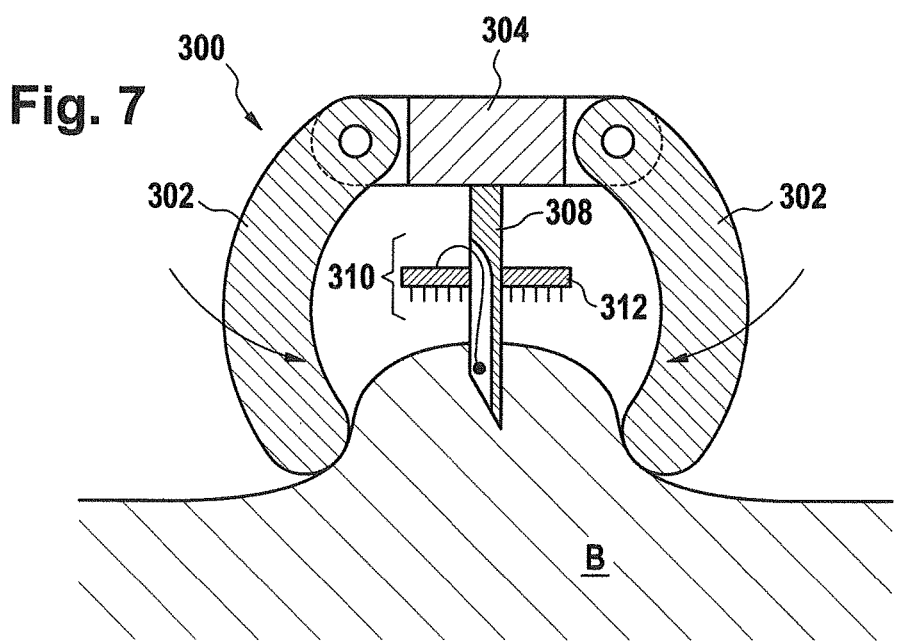
FIG. 7 shows a schematic sectional view of a fifth exemplary embodiment of a medical applicator.

According to FIG. 7, a fifth exemplary embodiment of a medical applicator may include a medical applicator 300 having an insertion needle 308 and a generalized lifting means for throwing up a limited and surface adjacent portion of the human or animal body B against the insertion needle 308. In a more detailed example, the lifting means may be realized as a number of pincer arms 302 configured to create an upwardly bending plication in the skin and subcutaneous tissue of the human or animal body B when being pushed together. The pincer arms 302 may be pivotable relative to a base member 304 carrying the insertion needle 308. In a much more detailed example, the pincer arms 302 may be hinge mounted to the base member 304, as shown. The pincer arms 302 may be manually actuated in a basic exemplary situation. Not shown in the drawing, an actuating means may be provided to enable semi-automatic or full-automatic operation of the pincer arms. An additional raising mechanism may be provided for raising the pincer arms 302 upwardly versus the insertion needle 308. It may be understood as an advantage of this approach to allow implementation for direct manual operation without necessity of additional manipulation units or similar expensive devices.

Additionally, the fifth exemplary embodiment as described before may be provided with means for supporting elastically and/or spring biased deployment operation in a manner analogous to the second exemplary embodiment of a medical applicator as described before. In particular, a pressure spring may be provided between the lower surface of the base member 304 and the upper surface of the external device 312 of the sensor assembly 310. In instances, a housing may be provided for receiving the pressure spring to prevent damage and/or contamination. The housing may be provided with a number of retention pins to maintain the pressure spring in a biased configuration. This configuration, as a result, would be very similar to the second exemplary embodiment as explained before. Alternatively, when a housing is considered disadvantageous for some reason, there may be provided a number of retention hooks extending from the base member 304 to the external device 312 of the sensor assembly 310. A number of hooking points may be provided on the top surface of the external device 312 to provide for secure engagement with the hooks.

Automatic deployment of the sensor assembly 310 may be achieved in a similar configuration by coupling the pincer arms 302 action to the retention pins or hooks, respective. In particular, there may be means to retract the retention pins or hooks, respective, when the pincer arms 302 approach to each other. Such automatic deployment would be useful as allowing single-handed operation of the device by a user. This may be advantageous in self-treatment situations when the sensor assembly has to be deployed to the back of the hand or the lower arm region.

LIST OF REFERENCE NUMERALS

100 Medical Applicator
102 Container Member
104 Cavity
106 Orifice
108 Insertion Needle
110 Sensor Assembly
112 External Device
114 Electrical Sensor
116 Sealing Member
118 Protective Liner
120 Suction Port
122 Piston Member
124 Spring
126 Volume
128 Retention Pin
130 Bellow
132 Needle Mount
200 Manipulation Unit
202 Casing
204 Fitting
206 Battery
208 Vacuum Pump 210 Port
212 Sealing Gasket
214 Electronic Controller
300 Medical Applicator
302 Pincer Arm
304 Base Member
308 Insertion Needle
310 Sensor Assembly
312 External Device

The invention claimed is:

1. A medical applicator comprising:
an insertion needle configured for puncturing a part of a human or animal body;
a sensor assembly configured to be at least partially inserted into the human or animal body when the human or animal body is punctured by said insertion needle; and
lifting means for lifting up a surface adjacent portion of the human or animal body towards said insertion needle, wherein said lifting means comprises a container member defining a cavity and an orifice, said cavity being configured for receiving said sensor assembly, said insertion needle being located within said cavity at a recessed position relative to the orifice and being configured for puncturing a part of said human or animal body entering through said orifice, said lifting means further comprising means for applying underpressure to said cavity for taking, through said orifice, an adjacent portion of said human or animal body into said cavity by suction, and wherein said sensor assembly comprises an external device configured to remain outside the human or animal body after deployment of said sensor assembly and having at least one self-adhesive surface portion facing towards said orifice.

2. The medical applicator according to claim 1, said medical applicator being configured to allow displacement of said insertion needle relative to said orifice towards said adjacent portion of said human or animal body.

3. The medical applicator according to claim 1, wherein said insertion needle is slidably movable relative to said container member.

4. The medical applicator according to claim 2, wherein said insertion needle is supported by a piston member, said piston member being slidably movable within a section of said container member and being exposable to an actuating force by means of a biased elastic member and/or by application of the underpressure.

5. The medical applicator according to claim 4, wherein said external device is admittable to the actuating force by means of the biased elastic member and/or by application of the underpressure for deployment of the external device to a surface of the human or animal body.

6. The medical applicator according to claim 5, wherein a fixation of said external device is releasable by deformation of a portion of the container member and/or by retraction of retention pins.

7. The medical applicator according to claim 1, wherein said external device is releasably fixed in a biased pre-deployment position.

8. The medical applicator according to claim 1, wherein said medical applicator includes a sealing member extending over said orifice to cover said cavity.

9. The medical applicator according to claim 1, whereby said lifting means comprises pincer arms configured for creating an upwardly bending movement of the skin and subcutaneous tissue of the human or animal body towards the insertion needle.

10. A system comprising:
a medical applicator comprising:
an insertion needle configured for puncturing a part of a human or animal body,
a sensor assembly configured to be at least partially inserted into the human or animal body when the human or animal body is punctured by said insertion needle, and
lifting means for lifting up a surface adjacent portion of the human or animal body towards said insertion needle, wherein
said lifting means comprises a container member defining a cavity and an orifice, said cavity being configured for receiving said sensor assembly, said insertion needle being located within said cavity at a recessed position relative to the orifice and being configured for puncturing a part of said human or animal body entering through said orifice, said lifting means further comprising means for applying underpressure to said cavity for taking, through said orifice, an adjacent portion of said human or animal body into said cavity by suction, and wherein
said sensor assembly comprises an external device configured to remain outside the human or animal body after deployment of said sensor assembly and having at least one self-adhesive surface portion facing towards said orifice; and
a manipulation unit for facilitating utilization of the medical applicator, said manipulation unit comprising a fitting for engagement with said medical applicator and means for generation of the underpressure and/or means for applying a force to the container member of the medical applicator received in said fitting for effecting deformation thereof.

11. The manipulation unit according to claim 10, wherein said means for generation of the underpressure comprises an electric vacuum pump.

12. The manipulation unit according to claim 10, further comprising puncturing means for puncturing the container member of the medical applicator received in the fitting to form a suction port for the application of the underpressure.

13. The manipulation unit according to claim 10, wherein said manipulation unit additionally comprises progress sensor means for detecting the presence of a portion of the human or animal body at an internal location within said cavity of said medical applicator and generating a signal descriptive thereto.

14. The manipulation unit according to claim 13, wherein said means for generation of the underpressure comprises a vacuum pump and said manipulation unit comprises an electronic controller configured for operating the vacuum pump in response to said signal of said progress sensor means.

* * * * *